United States Patent
Bourzat et al.

[11] 4,271,167
[45] Jun. 2, 1981

[54] HYDROXYALKYL PYRID-2-YL DITHIOCARBAMATES, THEIR PREPARATION AND THEIR USE

[75] Inventors: Jean-Dominique Bourzat, Paris; Daniel Farge, Thiais; André Léger, Paris; Gerard Ponsinet, Sucy-en-Brie, all of France

[73] Assignee: Rhone-Poulenc Industries, Paris, France

[21] Appl. No.: 94,288

[22] Filed: Nov. 14, 1979

[30] Foreign Application Priority Data

Nov. 16, 1978 [FR] France ................. 78 32388

[51] Int. Cl.³ .............. A61K 31/44; C07D 213/71
[52] U.S. Cl. .................... 424/263; 546/280; 546/305
[58] Field of Search ............... 546/305; 424/263

[56] References Cited

U.S. PATENT DOCUMENTS

| | | | |
|---|---|---|---|
| 3,725,422 | 4/1973 | Capps et al. | 546/305 O |
| 3,726,880 | 4/1973 | Capps et al. | 546/305 O |
| 3,732,216 | 5/1973 | Weinstock | 424/246 X |
| 4,039,550 | 8/1977 | Dickinson et al. | 546/305 O |
| 4,164,579 | 8/1979 | Bourzat et al. | 546/305 X |

Primary Examiner—John D. Randolph
Attorney, Agent, or Firm—Stevens, Davis, Miller & Mosher

[57] ABSTRACT

New dithiocarbamates of the formula:

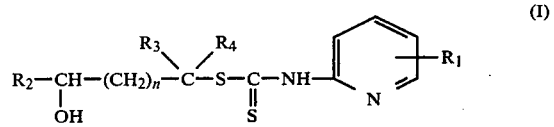

(I)

in which $R_1$ is hydrogen or halogen in the 4-, 5- or 6-position, n is equal to 0 or 1, $R_2$ represents hydrogen or various aliphatic or aromatic radicals which may be substituted, $R_3$ represents hydrogen or various aliphatic radicals, and $R_4$ represents a hydrogen atom or an alkyl radical, their optically active forms, and their salts, when such salts exist, are valuable anthelmintic agents. They may be made inter alia by reduction of the corresponding ketones.

9 Claims, No Drawings

HYDROXYALKYL PYRID-2-YL DITHIOCARBAMATES, THEIR PREPARATION AND THEIR USE

DESCRIPTION

This invention relates to hydroxyalkyl pyrid-2-yldithiocarbamates, a process for their preparation, and pharmaceutical compositions containing them.

The present invention provides, as new compounds, the hydroxyalkyl pyrid-2-yldithiocarbamates of the formula:

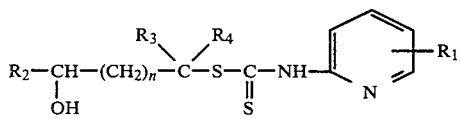
(I)

wherein $R_1$ represents a hydrogen or halogen atom in the 4-, 5- or 6- position and either (1) n is equal to 0, and (a) $R_2$ represents an alkyl radical containing 2 to 4 carbon atoms, which is substituted in a position other than the 1-position by amino, alkylamino, dialkylamino radical in which the alkyl parts can form, together with the nitrogen atom to which they are attached, a saturated heterocyclic ring with 5 or 6 ring members, which may contain another heteroatom chosen from oxygen, sulphur and a secondary or tertiary nitrogen atom, carbamoyl, alkylcarbamoyl, dialkylcarbamoyl, in which the alkyl parts can form, together with the nitrogen atom to which they are attached, a saturated heterocyclic ring as aforesaid or cyano, a dialkoxymethyl radical, phenylthiomethyl, 1-phenylcyclopropyl, 1-methylcyclohexyl, a phenyl radical which is substituted by an amino radical in the 2-position or by two identical radicals chosen from hydroxyl, methyl and methoxy, naphth-1-yl, or pyrid-4-yl, and $R_3$ and $R_4$ each represent a hydrogen atom, or (b) $R_2$ represents a hydrogen atom, an alkyl radical containing 1 to 8 carbon atoms, an alkyl radical containing 1 to 4 carbon atoms which is substituted by 1 to 3 halogen atoms or by phenyl, hydroxyl, alkoxy, alkylthio, carboxyl, alkoxycarbonyl, alkoxycarbonylalkoxy, alkoxycarbonylalkylthio, alkanoyloxy, alkanoyloxyalkoxy or alkanoyloxyalkylthio, a cycloalkyl radical of 3 to 6 carbon atoms, cyclohexenyl, a phenyl radical which is unsubstituted or substituted by a halogen atom or by an alkyl, alkoxy, hydroxyl or nitro radical, thien-2-yl, or an alkoxycarbonyl radical, $R_3$ represents a hydrogen atom or an alkyl, alkanoyloxyalkyl, alkoxycarbonylalkyl or alkoxycarbonyl radical or forms, together with $R_2$, an alkylene radical containing 3 or 4 carbon atoms, in the chain of which 2 adjacent carbon atoms can form part of a benzene ring, and $R_4$ represents a hydrogen atom or an alkyl radical; or alternatively (2) n is equal to 1, and $R_2$ represents a hydrogen atom, an alkyl radical or a phenyl radical which is unsubstituted or substituted by 1 or 2 identical substituents chosen from halogen atoms or hydroxyl, alkyl, alkoxy, alkylthio, nitro and amino radicals, and $R_3$ and $R_4$ each represent a hydrogen atom, it being understood that the abovementioned alkyl, alkoxy, and alkanoyl radicals are linear or branched and that, unless otherwise stated, they contain from 1 to 4 carbon atoms; and, when they exist, the optical isomers, metal salts, addition salts with nitrogen-containing bases, and acid addition salts of the aforesaid compounds.

According to a feature of the invention, the compounds of formula (I) can be prepared by reducing, in an alkaline medium, a compound of the formula:

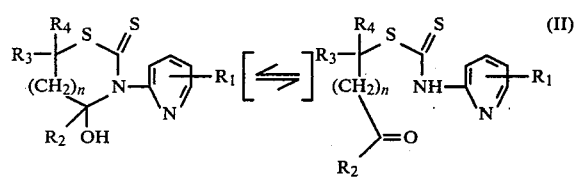
(II)

in which $R_1$, $R_2$, $R_3$, $R_4$ and n are as defined above, by any method which is in itself known for reducing a ketone group without affecting the rest of the molecule.

The reduction is generally carried out by the action of an alkali metal borohydride (e.g. potassium borohydride), optionally in the presence of a base such as sodium hydroxide, in an aqueous-organic medium [e.g. in a water/alcohol (water/methanol) mixture or in a water/acetonitrile mixture], at a temperature between 0° and 50° C.

The compound of the formula (II) can be obtained by reacting a compound of the formula:

(III)

[in which $R_2$ is as defined above, and (a) if it is desired to obtain a compound of the formula (II) in which n is equal to 0, $R_5$ represents a radical of the formula:

(IV)

in which $R_3$ and $R_4$ are as defined above and Hal represents a halogen atom, preferably a chlorine or bromine atom, or (b) if it is desired to obtain a compound of the formula (II) in which n is equal to 1, $R_5$ represents vinyl, 2-bromoethyl, 2-chloroethyl or 2-trimethylammonioethyl (the compound (III) being in the form of a salt if $R_5$ represents a 2-trimethylammonioethyl radical or, if desired, when $R_2$ represents a carboxyalkyl radical)] with a dithiocarbamate of the formula:

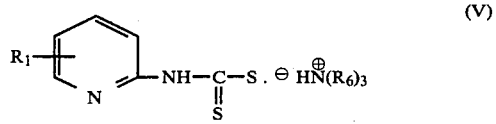
(V)

[in which $R_1$ is defined as above and the symbols $R_6$, which are identical or different, each represent an alkyl radical containing 1 to 4 carbon atoms].

In general, the reaction is carried out in an organic solvent (such as dimethylformamide, acetonitrile or chloroform), in water or in an aqueous-organic medium (e.g. in a water/dimethylformamide or water/acetonitrile mixture), at a temperature between −10° and +50° C.

The dithiocarbamates of the formula (V) can be obtained, in accordance with the method described by E. B. KNOTT, J. Chem. Soc., 1,644–9 (1956), by reacting carbon disulphide, in the presence of a tertiary amine, with a 2-aminopyridine of the formula:

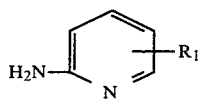

(VI)

in which $R_1$ is defined as above, or in accordance with the method described by D. B. CAPPS in U.S. Pat. No. 3,726,880.

The compounds of the formula (III) can be prepared by applying various general methods described in the literature, which are referred to in greater detail in the Examples.

Alternatively, the compounds of the formula (I) in which $R_1$ is as defined above, $R_2$ represents a hydrogen atom and, if n is equal to 0, $R_3$ and $R_4$ represent hydrogen atoms or alkyl radicals, or, if n is equal to 1, $R_3$ and $R_4$ represent hydrogen atoms, can also be obtained by reducing a compound of the formula:

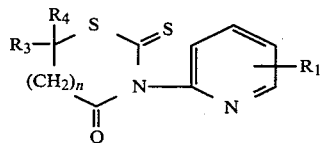

(VII)

in which $R_1$, $R_3$, $R_4$ and n are as defined above.

The reaction is generally carried out under the conditions described above for obtaining the compounds of formula (I) from the compound of formula (II).

The compounds of formula (VII) can be prepared by applying the method described by E. B. KNOTT, J. Chem. Soc., 1,648 (1956), or the method described in U.S. Pat. No. 3,732,216.

According to a further feature of the invention, the compounds of formula (I) in which n is equal to 0, $R_1$ is as defined above, $R_2$ represents a hydrogen atom, an alkyl radical containing 1 to 8 carbon atoms, an alkyl radical containing 1 to 4 carbon atoms, which is substituted by a hydroxyl, alkoxy or alkylthio radical, a phenyl radical which is unsubstituted or substituted by a halogen atom or by an alkyl, alkoxy, hydroxyl or nitro radical, or thien-2-yl, and $R_3$ and $R_4$ represents hydrogen atoms, can also be obtained by reacting a dithiocarbamate of the formula (V) with an epoxide of the formula:

(VIII)

in which $R_2$ is as defined above.

The reaction is generally carried out in an anhydrous organic solvent, such as acetonitrile, at a temperature of about 20° C.

The present invention includes within its scope the optical isomers of the compounds of formula (I), when such isomers exist. These optical isomers may be obtained by applying known methods. For example, they can be obtained by resolving an ester of the racemic product of the formula (I) with an optically active acid such as malic, mandelic, α-methoxyphenylacetic, α-trifluoromethylphenylacetic or (−)-menthoxyacetic acid.

Alternatively, they can be obtained by resolving a monoester of the racemic product of the formula (I) and of a dicarboxylic acid such as phthalic acid or succinic acid. The resolution is effected by forming a salt with an optically active base and carrying out successive crystallisations. The optically active base used is, e.g., strychnine, brucine, methylbenzylamine or dehydroabietylamine.

If it is desired to obtain the optically active forms of a product of the formula (I) in which $R_2$ represents an alkyl radical which is substituted by a hydroxyl or carboxyl radical, or a phenyl radical which is monosubstituted or disubstituted by a hydroxyl radical, the hydroxyl or carboxyl radical of the radical $R_2$ of the racemic product of the formula (I) is preferably protected beforehand.

If desired, the compounds of the present invention can be purified by physical methods such as crystallisation or chromatography.

If $R_2$ represents a carboxyalkyl radical, the new compounds can optionally be converted into metal salts or into addition salts with a nitrogen-containing base. These salts can be obtained by reaction with a metal base (especially an alkali metal base or alkaline earth metal base), ammonia or a nitrogen-containing base, in a suitable solvent such as an alcohol, an ether or water, or by an exchange reaction with a salt of an organic acid. The salt formed precipitates after concentration, if necessary, of its solution; it is separated by filtration or decantation.

If $R_2$ represents an alkyl radical which is substituted [by amino, alkylamino or dialkylamino (in which the alkyl parts can form, together with the nitrogen atom to which they are attached, the heterocyclic ring defined above) or a dialkylcarbamoyl radical in which the alkyl parts form, together with the nitrogen atom to which they are attached, a saturated heterocyclic ring with 5 or 6 ring members, containing another secondary or tertiary nitrogen atom], aminophenyl or diaminophenyl, the compounds of the invention can also be converted into addition salts with acids. The addition salts can be obtained by reacting the compounds with acids, in suitable solvents; organic solvents used are, e.g., alcohols, ketones, ethers or chlorinated solvents. The salt formed precipitates after concentration, if necessary, of the solution; it is separated by filtration or decantation.

The new products according to the present invention, their optical isomers, and their salts if appropriate, are particularly active as anthelmintics having a broad spectrum of action against nematodes.

Their activity has been demonstrated, especially against *Nematospiroides dubius* in mice, at doses of between 5 and 100 mg/kg, administered orally.

Furthermore, some of the compounds of the invention have shown themselves to be active against filariosis in cotton rats caused by *Litomosoides carinii*, at doses of between 25 and 50 mg/kg per day, administered orally, for a treatment lasting 5 consecutive days.

The toxicity to mice of the compounds of the invention, expressed as their 50% lethal dose ($LD_{50}$), is between 200 mg/kg and a value of more than 1,000 mg/kg, administered orally.

Of particular value are the compounds in which $R_1$ represents a hydrogen or halogen atom in the 5-position and n is equal to 0, $R_2$ represents a hydrogen atom or an alkyl radical containing 1 to 4 carbon atoms (which is optionally substituted by an hydroxy, alkylthio or alkoxycarbonyl radical) or a phenyl radical (which is optionally substituted by a halogen atom or by a methyl radical) and $R_3$ and $R_4$ represent hydrogen atoms or methyl radicals, or alternatively n is equal to 1 and $R_2$ represents a hydrogen atom, an alkyl radical containing 1 to 4 carbon atoms or a phenyl radical (which is optionally substituted by a halogen atom or by a methyl radical).

Amongst these compounds, those which are more especially valuable for their good activity against *Nematospiroides dubius* are the compounds in which n is equal to 0 or 1, $R_3$ and $R_4$ represent hydrogen atoms and, if $R_1$ represents a hydrogen or chlorine atom in the 5-position, $R_2$ represents a phenyl radical, or alternatively, if $R_1$ represents a chlorine atom in the 5-position, $R_2$ represents a hydrogen atom or a methyl radical or a phenyl radical which is substituted by a fluorine atom or by a methyl radical.

Amongst these compounds, those which are more particularly active are those in which $R_1$ is a chlorine atom in the 5-position, $R_3$ and $R_4$ are hydrogen atoms and, if n is equal to 0, $R_2$ represents a hydrogen atom or a phenyl radical which is unsubstituted or substituted by a fluorine atom, or alternatively, if n is equal to 1, $R_2$ represents a methyl radical or a phenyl radical which is optionally substituted by a fluorine atom.

The products which are more especially valuable for their good anti-filariosis activity are those in which $R_1$, $R_3$ and $R_4$ represent hydrogen atoms and, if n is equal to 0, $R_2$ represents a hydrogen atom or a hydroxymethyl or methylthiomethyl radical, or alternatively, if n is equal to 1, $R_2$ represents a hydrogen atom.

When the compounds of formula I are used in human or veterinary therapy in the form of salts, the anion or cation present in such salts (in addition to the cation or anion provided by the compound of formula I respectively) must be such as not to interfere with the desired properties of the compound of formula I and in particular must be pharmaceutically acceptable (non-toxic) at the dosage used. Examples of pharmaceutically acceptable salts which may be mentioned are the salts with alkali metals (such as the potassium, sodium or lithium salts) or with alkaline earth metals, the ammonium salts, the salts of nitrogen-containing bases (e.g. ethanolamine or lysine) and the addition salts with mineral acids (such as the hydrochlorides, sulphates, nitrates or phosphates) or organic acids (such as the acetates, propionates, succinates, benzoates, fumarates, maleates, theophylline-acetates, salicylates, phenolphthaleinates, methylene-bis-β-oxynaphthoates or substitution derivatives of these compounds).

The following Examples illustrate the invention.

EXAMPLE 1

A 4 N aqueous solution of sodium hydroxide (150 cc) is added, at a maximum of 20° C., to a suspension of 4-hydroxy-3-(pyrid-2-yl)-thiazolidine-2-thione (127.5 g) in methanol (900 cc), and a solution of potassium borohydride (33.0 g) in water (150 cc) is then added at a maximum of 20° C. The reaction is allowed to proceed for 1 hour at 20° C. A 4 N aqueous solution of hydrochloric acid (300 cc) is added at a maximum of 20° C. The methanol is evaporated off under reduced pressure (20 mm Hg) at 45° C. The aqueous phase is extracted 3 times with methylene chloride (2.5 liters in total). The organic solution is washed 3 times with distilled water (1.5 liters in total), dried over sodium sulphate and evaporated. The resulting product (110.0 g) is purified by recrystallisation from a mixture of acetonitrile (100 cc) and isopropyl ether (200 cc). After drying under reduced pressure (0.2 mm Hg) at 40° C., 2-hydroxyethyl pyrid-2-yldithiocarbamate (85.1 g), which melts at 88° C., is obtained.

4-Hydroxy-3-(pyrid-2-yl)-thiazolidine-2-thione can be prepared in accordance with the following procedure.

A 50% by weight aqueous solution of chloroacetaldehyde (37.7 g) is added at 10° C., to a solution of triethylammonium pyrid-2-yldithiocarbamate (65.4 g) in dimethylformamide (300 cc). The reaction is allowed to proceed for 16 hours at 20° C. After evaporating off the solvents under pressure (0.1 mm Hg) at 50° C., the residual oil is treated with chloroform (750 cc). The chloroform solution is washed twice with distilled water (200 cc in total), dried over sodium sulphate and evaporated. The oily residue (38 g) is dissolved in boiling ethanol (180 cc), and boiling isopropyl ether (180 cc) and decolourising charcoal (1 g) are added. After filtering the boiling solution and then cooling for 2 hours at 2° C., the crystals which have appeared are filtered off, washed with an ice-cooled mixture (50 cc in total) of ethanol (25 cc) and isopropyl ether (25 cc) and dried under reduced pressure (0.1 mm Hg) at 45° C. 4-Hydroxy-3-(pyrid-2-yl)thiazolidine-2-thione (17.8 g), which melts at 110° C., is thus obtained.

Triethylammonium pyrid-2-yldithiocarbamate (m.p.=95° C.) is prepared in accordance with the method described by E. B. KNOTT, J. Chem. Soc., 1,644–9 (1956).

EXAMPLE 2

The procedure of Example 1 is followed, but a solution of 5,5-dimethyl-4-hydroxy-3-(pyrid-2-yl)-thiazolidine-2-thione (4.8 g) and a 4.16 N aqueous solution of sodium hydroxide (4.8 cc) in methanol (30 cc), and a solution of potassium borohydride (1.1 g) in distilled water (5 cc), are used as the starting materials at a maximum of 20° C. The reaction is allowed to proceed for 18 hours at 20° C. After recrystallisation from isopropyl ether (15 cc), 1-hydroxy-2-methylprop-2-yl pyrid-2-yldithiocarbamate (1.0 g), which melts at 130° C., is obtained.

5,5-Dimethyl-4-hydroxy-3-(pyrid-2-yl)-thiazolidine-2-thione can be prepared in the following manner 2-Bromo-2-methylpropanol (39.7 g) is added, at about 5° C., to a suspension of triethylammonium pyrid-2-yldithiocarbamate (71.2 g) in anhydrous acetonitrile (330 cc). The reaction is allowed to proceed for 1 hour at 20° C. The insoluble triethylamine hydrobromide is removed by filtration. The acetonitrile is evaporated off under reduced pressure (20 mm Hg) at 40° C. The residual oil is treated with methylene chloride (300 cc). The organic solution is washed twice with distilled water (100 cc in total), dried over sodium sulphate and evaporated. The resulting product (60 g) is dissolved in methylene chloride (300 cc), and the solution is filtered through silica (0.2–0.5 mm., 850 g) contained in a column of diameter 5 cm. Elution is carried out with methylene chloride (9 liters). After evaporating off the solvent under reduced pressure (20 mm Hg) at 40° C., the resulting product (50 g) is dissolved in boiling methylcyclohexane (150 cc). After cooling for 16 hours at 2° C., the crystals which have appeared are filtered off, washed with methylcyclohexane (50 cc) and dried under reduced pressure (0.1 mm Hg) at 40° C. 5,5-Dimethyl-4-hydroxy-3-(pyrid-2-yl)-thiazolidine-2-thione (44.1 g), which melts at 80° C., is thus obtained.

2-Bromo-2-methylpropanal (b.p.=112° C./760 mm Hg) is prepared in accordance with the method described by C. L. STEVENS and B. T. GILUS, J. Amer. Chem. Soc., 79, 3,448 (1957).

EXAMPLE 3

A solution of potassium borohydride (5.4 g) in distilled water (80 cc) is added, at a maximum of 35° C., to a solution of 4-hydroxy-4-methyl-3-(pyrid-2-yl)-thiazolidine-2-thione (22.6 g) in methanol (320 cc). The reaction is allowed to proceed for 30 minutes at 25°–35° C. A 3 N aqueous solution of hydrochloric acid (33.2 cc) is added. The methanol is evaporated off under reduced pressure (20 mm Hg) at 45° C. The aqueous phase is extracted with ethyl ether (800 cc). The ether solution is washed twice with distilled water (300 cc in total), treated with decolourising charcoal (1 g), dried over sodium sulphate and evaporated. The resulting product (23.0 g) is purified by recrystallisation from a mixture of ethyl ether (100 cc) and isopropyl ether (100 cc). 2-Hydroxypropyl pyrid-2-yldithiocarbamate (11.1 g), which melts at 78° C., is obtained.

4-Hydroxy-4-methyl-3-(pyrid-2-yl)-thiazolidine-2-thione can be prepared in the following manner The procedure of Example 1 is followed, but triethylammonium pyrid-2-yldithiocarbamate (40.6 g) and chloroacetone (14.0 g) in distilled water (250 cc) are used as the starting materials at 20° C. The reaction is allowed to proceed for 2 hours at 20° C. After recrystallisation from ethanol (40 cc), 4-hydroxy-4-methyl-3-(pyrid-2-yl)-thiazolidine-2-thione (20.0 g), which melts at 122° C., is obtained.

EXAMPLE 4

A solution of potassium borohydride (5.4 g) in distilled water (35 cc) is added, at a maximum of 20° C., to a suspension of 4-hydroxy-4-hydroxymethyl-3-(pyrid-2-yl)-thiazolidine-2-thione (23.8 g) in anhydrous acetonitrile (240 cc). The reaction is allowed to proceed for 30 minutes at 20° C. An 8.5 N aqueous solution of hydrochloric acid (12 cc) is added at a maximum of 20° C. The acetonitrile is evaporated off under reduced pressure (20 mm Hg) at 45° C. The aqueous phase is extracted 3 times with chloroform (500 cc in total). The organic solution is washed with distilled water (100 cc), dried over sodium sulphate and evaporated. The resulting product (21.2 g) is purified by crystallisation from a mixture of methylene chloride (100 cc) and isopropyl ether (50 cc). After drying in the atmosphere for 16 hours, yellow crystals (13 g), which melt at 96° C., are obtained and these are purified again by recrystallisation from a boiling mixture of acetonitrile (75 cc) and isopropyl ether (20 cc). After filtering the boiling solution and then cooling for 2 hours at 2° C., the crystals which have appeared are filtered off, washed with an ice-cooled mixture (25 cc in total) of acetonitrile (20 cc) and isopropyl ether (5 cc) and dried under reduced pressure (0.1 mm Hg) at 45° C. 2,3-Dihydroxy-propyl pyrid-2-yldithiocarbamate (10.2 g), which melts at 98° C., is thus obtained.

4-Hydroxy-4-hydroxymethyl-3-(pyrid-2-yl)-thiazolidine-2-thione can be prepared in accordance with the following procedure A 5.5 N aqueous solution of sodium hydroxide (36 cc) is added in the course of 5 minutes, at 22°–23° C., to a suspension of 3-chloro-2-oxopropyl acetate (29.9 g) in distilled water (500 cc). The hydrolysis reaction is allowed to proceed for 15 minutes at 22° C. and triethylammonium pyrid-2-yldithiocarbamate (53.6 g) is then added in the course of 5 minutes at a maximum of 23° C. The reaction is allowed to proceed for 2 hours at 20°–23° C. The crystals which have appeared are filtered off, washed with distilled water (50 cc) and then with ethyl ether (50 cc) and dried under reduced pressure (0.1 mm Hg) at 45° C. 4-Hydroxy-4-hydroxymethyl-3-(pyrid-2-yl)-thiazolidine-2-thione (12.0 g), which melts at 134°–135° C., is thus obtained.

3-Chloro-2-oxopropyl acetate (b.p.=129°–131° C./25 mm Hg) is prepared in accordance with the method described by E. R. CURK and J. B. G. HOWES, J. Chem. Soc., 1,152 (1956). Triethylammonium pyrid-2-yldithiocarbamate (m.p.=95° C.) is prepared in accordance with method described by E. B. KNOTT, J. Chem. Soc., 1,644–9 (1956).

EXAMPLE 5

The procedure of Example 3 is followed, but a suspension of 4-hydroxy-4-methylthiomethyl-3-(pyrid-2-yl)-thiazolidine-2-thione (13.6 g) in methanol (160 cc) and a solution of potassium borohydride (2.7 g) in distilled water (40 cc) are used as the starting materials at a maximum of 30° C. The reaction is allowed to proceed for 150 minutes at between 20° and 30° C. The crude product (13.5 g) is dissolved in a mixture of cyclohexane (80 cc) and ethyl acetate (20 cc). The solution is chromatographed on silica (0.2–0.5 mm, 300 g) contained in a column of diameter 4 cm. Elution is carried out first with a mixture of cyclohexane (800 cc) and ethyl acetate (200 cc), this eluate being discarded, and then with a mixture of cyclohexane (1,600 cc) and ethyl acetate (450 cc), this eluate being collected and evaporated under reduced pressure (20 mm Hg) at 45° C. and then dried under reduced pressure (0.2 mm Hg) at 50° C. 2-Hydroxy-3-methylthiopropyl pyrid-2-yldithiocarbamate (12.3 g) is obtained.

NMR spectrum (60 MHz) run on an approximately 10% solution in deuterated chloroform:

| | | |
|---|---|---|
| 2.15 ppm: | singlet (3H) | $S-CH_3$ |
| 2.4 to 3.1 ppm: | multiplet (2H) | $-CH_2-SCH_3$ |
| 3.0 to 3.9 ppm: | multiplet (2H) | $-CSS-CH_2-$ |
| 4.1 ppm: | multiplet (1H) | $-CH(OH)-$ |
| 5.6 to 7.4 ppm: | broad hump (1H) | $-OH$ |
| 7.15 ppm: | doublet of doublets (1H) J = 7; 5 | $-H_5$ (pyridine) |
| 7.8 ppm: | doublet of triplets (1H) J = 7; 1.5 | $-H_4$ (pyridine) |
| 8.4 ppm: | doublet of doublets (2H) J = 5; 1.5 | $-H_6$ (pyridine) |
| 8.5 ppm: | doublet J = 3.5 | $-H_3$ (pyridine) |
| not detected: | (1H) | $-NH-$ |

4-Hydroxy-4-methylthiomethyl-3-(pyrid-2-yl)-thiazolidine-2-thione can be prepared in the following manner The procedure of Example 1 is followed, but triethylammonium pyrid-2-yldithiocarbamate (43.5 g) and 1-chloro-3-methylthiopropan-2-one (22.2 g) in distilled water (200 cc) are used as the starting materials at a maximum of 25° C. The reaction is allowed to proceed for 2 hours at 20°–25° C. After recrystallisation from ethanol (100 cc), 4-hydroxy-4-methylthiomethyl-3-(pyrid-2-yl)-thiazolidine-2-thione (27.0 g), which melts at 104° C., is obtained.

1-Chloro-3-methylthiopropan-2-one (b.p.=98°-100° C./28 mm Hg) (22.5 g) is obtained by reacting diazomethane (22.4 g) with methylthioacetyl chloride (40.1 g) in ethyl ether (300 cc) at between −10° C. and 0° C. and then reacting an aqueous solution of hydrochloric acid (d=1.19, 35 cc) with the resulting mixture at between 0° and 5° C.

Methylthioacetyl chloride (b.p.=66° C./30 mm Hg) is prepared in accordance with the method described by A. MOORADIAN et al., J. Amer. Chem. Soc., 71, 3,372 (1949).

EXAMPLE 6

The procedure of Example 3 is followed, but a solution of methyl 3-[4-hydroxy-3-(pyrid-2-yl)-2-thioxothiazolidin-4-yl]-propionate (18.0 g) in methanol (200 cc) and a solution of potassium borohydride (3.25 g) in distilled water (50 cc) are used as the starting materials at a maximum of 5° C. The reaction is allowed to proceed for 2 hours at between 2° and 5° C. The crude product (17.0 g) is dissolved in a mixture of chloroform (80 cc) and ethyl acetate (20 cc). The solution is chromatographed on silica (0.063-0.2 mm) (350 g) contained in a column of diameter 4.2 cm. Elution is carried out with a mixture of chloroform (1,200 cc) and ethyl acetate (300 cc), this eluate being discarded, and then with a mixture of chloroform (2,800 cc) and ethyl acetate (700 cc), this eluate being collected and evaporated under reduced pressure (20 mm Hg) at 45° C. and then dried under reduced pressure (0.2 mm Hg) at 50° C. 2-Hydroxy-4-methoxycarbonylbutyl pyrid-2-yldithiocarbamate (13.2 g) is obtained.

NMR spectrum (60 MHz) run on an approximately 10% solution in deuterated chloroform:

| | | |
|---|---|---|
| 1.6 to 2.1 ppm: | multiplet (2H) | —CH(OH)—CH$_2$ |
| 2.53 ppm: | multiplet (2H) | —CH$_2$—COOCH$_3$ |
| 3.1 to 3.9 ppm: | multiplet (5H) | —CSSCH$_2$— |
| 3.7 ppm: | singlet | —OCH$_3$ |
| 4.05 ppm: | multiplet (1H) | —CH(OH) |
| 7.15 ppm: | doublet of doublets (1H) J = 7.5; 5; 1 | —H$_5$ (pyridine) |
| 7.75 ppm: | doublet of triplets (1H) J = 7.5; 2 | —H$_4$ (pyridine) |
| 8.45 ppm: | doublet of doublets (2H) | J = 5; 2 | —H$_6$ (pyridine) |
| 8.55 ppm: | doublet of doublets | J = 7.5; 1 | —H$_3$ (pyridine) |
| 0 to 10 ppm: | not detected (2H) | —NH— and —OH |

Methyl 3-[4-hydroxy-3-(pyrid-2-yl)-2-thioxothiazolidin-4-yl]-propionate can be prepared in the following manner: The procedure of Example 1 is followed, but triethylammonium pyrid-2-yldithiocarbamate (54.0 g) and methyl 5-bromo-4-oxopentanoate (42.0 g) in distilled water (250 cc) are used as the starting materials at a maximum of 25° C. The reaction is allowed to proceed for 1 hour at 20°-25° C. After recrystallisation from a mixture of ethanol (60 cc) and isopropyl ether (120 cc), methyl 3-[4-hydroxy-3-(pyrid-2-yl)-2-thioxothiazolidin-4-yl]-propionate (42.0 g), which melts at 75° C., is obtained.

Methyl 5-bromo-4-oxopentanoate (b.p.=84°-85° C./0.1 mm Hg) is prepared in accordance with the method described by H. DANNENBERG and S. LÄUFER, Chem. Ber., 89, 2,242 (1956).

EXAMPLE 7

The procedure of Example 3 is followed, but a suspension of 4-hydroxy-4-phenyl-3-(pyrid-2-yl)-thiazolidine-2-thione (23.0 g) in methanol (240 cc) and a solution of potassium borohydride (4.3 g) in distilled water (60 cc) are used as the starting materials at a maximum of 35° C. The reaction is allowed to proceed for 30 minutes at 25°-35° C. The crude product (26.1 g) is dissolved in a mixture of cyclohexane (200 cc) and ethyl acetate (50 cc). The solution is chromatographed on silica (0.2-0.5 mm) (280 g) contained in a column of diameter 4 cm. Elution is carried out with a mixture of cyclohexane (480 cc) and ethyl acetate (120 cc) and then with a mixture of cyclohexane (280 cc) and ethyl acetate (120 cc), these eluates being discarded. Elution is continued with a mixture of cyclohexane (700 cc) and ethyl acetate (300 cc), this eluate being collected and evaporated to dryness under reduced pressure (20 mm Hg) at 45° C. The chromatographed product (18.1 g) is purified by recrystallisation from a mixture of ethyl ether (90 cc) and petroleum ether (b.p. 40° to 65° C., 30 cc). 2-Hydroxy-2-phenylethyl pyrid-2-yldithiocarbamate (14.9 g), which melts at 82° C., is obtained.

4-Hydroxy-4-phenyl-3-(pyrid-2-yl)-thiazolidine-2-thione can be prepared in the following manner The procedure of Example 2 is followed, but triethylammonium pyrid-2-yldithiocarbamate (201.5 g) and phenacyl bromide (148 g) in anhydrous acetonitrile (1,600 cc) are used as the starting materials at between 18° and 25° C. The reaction is allowed to proceed for 2 hours at 20°-25° C. After recrystallisation from ethanol (2,000 cc), 4-hydroxy-4-phenyl-3-(pyrid-2-yl)-thiazolidine-2-thione (168.1 g), which melts at 135° C., is obtained.

When the product is examined by I.R. spectroscopy in bromoform solution, about 10% of phenacyl pyrid-2-yl-dithiocarbamate is observed (carbonyl band at 1,685 cm$^{-1}$). This band is not observed when the product is examined between plates in petroleum jelly.

EXAMPLE 8

A solution of potassium borohydride (8.35 g) in distilled water (95 cc) is added, at a maximum of 30° C., to a suspension of 3-(5-chloropyrid-2-yl)-4-hydroxythiazolidine-2-thione (38.0 g) in acetonitrile (380 cc). The reaction is allowed to proceed for 30 minutes at between 25° and 30° C. A 3 N aqueous solution of hydrochloric acid (51 cc) is added at a maximum of 20° C. The acetonitrile is evaporated off under reduced pressure (20 mm Hg) at 45° C. The resulting crystals are filtered off, washed with acetonitrile (15 cc) and isopropyl ether (25 cc) and then 4 times with distilled water (250 cc in total) and dried in air at 20° C. The resulting product (23.7 g; m.p.=100° C.) is suspended in chloroform (480 cc). The suspension is chromatographed on silica (0.2-0.5 mm) (240 g) contained in a column of diameter 3.8 cm. Elution is carried out with chloroform (400 cc) and then with a mixture of chloroform (1,380 cc) and methanol (35 cc), this eluate being discarded. Elution is continued with a mixture of chloroform (720 cc) and methanol (80 cc), this eluate being collected and evaporated to dryness under reduced pressure (20 mm Hg) at 45° C. The resulting crystals are washed with isopropyl ether (60 cc) and then with ice-cooled acetonitrile (10 cc) and dried under reduced pressure (0.2 mm Hg) at 45° C. 2-Hydroxyethyl 5-chloropyrid-2-yldithiocarbamate (18.5 g), which melts at 108° C., is thus obtained.

3-(5-Chloropyrid-2-yl)-4-hydroxythiazolidine-2-thione can be prepared by the procedure described in Example 1, using a 50% by weight aqueous solution of chloroacetaldehyde (23.6 g) and triethylammonium 5-chloropyrid-2-yl-dithiocarbamate (46.0 g) in anhydrous acetonitrile (350 cc) as the starting materials at between 2° and 20° C., the reaction being carried out for 3 hours. After recrystallisation from acetonitrile (80 cc), 3-(5-chloropyrid-2-yl)-4-hydroxythiazolidine-2-thione (22.0 g), which melts at 133° C., is obtained.

EXAMPLE 9

The procedure of Example 1 is followed, but a suspension of 3-(5-chloropyrid-2-yl)-4-hydroxy-5,5-dimethylthiazolidine-2-thione (2.75 g) in methanol (30 cc) and a 4.16 N aqueous solution of sodium hydroxide (2.4 cc), and a solution of potassium borohydride (0.54 g) in distilled water (3 cc), are used as the starting materials at a maximum of 20° C. The reaction is allowed to proceed for 18 hours at 20° C. After recrystallisation of the product from acetonitrile (15 cc), 1-hydroxy-2-methylprop-2-yl 5-chloropyrid-2-yldithiocarbamate (0.8 g), which melts at 140° C., is obtained.

3-(5-Chloropyrid-2-yl)-4-hydroxy-5,5-dimethylthiazolidine-2-thione can be prepared as in Example 1, using 2-bromo-2-methylpropanol (45.5 g) and triethylammonium 5-chloropyrid-2-yldithiocarbamate (91.0 g) in anhydrous acetonitrile (500 cc) as the starting materials at between 20° and 25° C., the reaction being carried out for 18 hours. After recrystallisation from ethyl acetate (250 cc), 3-(5-chloropyrid-2-yl)-4-hydroxy-5,5-dimethylthiazolidine-2-thione (37.0 g), which melts at 140° C., is obtained.

EXAMPLE 10

The procedure of Example 3 is followed, but a suspension of 3-(5-chloropyrid-2-yl)-4-hydroxy-4-methylthiazolidine-2-thione (20.0 g) in methanol (200 cc) and a solution of potassium borohydride (4.15 g) in distilled water (50 cc) are used as the starting materials at a maximum of 30° C. The reaction is allowed to proceed for 30 minutes at between 25° and 30° C. After recrystallisation from acetonitrile (60 cc), 2-hydroxypropyl 5-chloropyrid-2-yldithiocarbamate (17.3 g), which melts at 114° C., is obtained.

3-(5-Chloropyrid-2-yl)-4-hydroxy-4-methylthiazolidine-2-thione can be prepared in the following manner: Chloroacetone (13.5 g) is added, at 2° C., to a suspension of triethylammonium 5-chloropyrid-2-yldithiocarbamate (44.5 g) in dimethylformamide (180 cc). The reaction is allowed to proceed for 45 minutes at 2° C. The insoluble triethylamine hydrochloride is removed by filtration and washed with dimethylformamide (20 cc). The dimethylformamide (filtrate and washings) is evaporated off under reduced pressure (0.1 mm Hg) at 45° C. and the residual oil is treated with ethyl acetate (400 cc). The organic solution is washed twice with distilled water (100 cc in total), dried over sodium sulphate and evaporated. The resulting product (41 g) is dissolved in boiling ethanol (100 cc). After cooling for 4 hours at 2° C., the crystals which have appeared are filtered off, washed twice with ice-cooled ethanol (15 cc in total), and dried under reduced pressure (0.1 mm Hg) at 45° C. 3-(5-Chloropyrid-2-yl)-4-hydroxy-4-methylthiazolidine-2-thione (16.8 g), which melts at 95° C., is thus obtained.

Triethylammonium 5-chloropyrid-2-yldithiocarbamate (m.p. = 130° C.) is prepared in accordance with the method described by D. B. CAPPS in U.S. Pat. No. 3,726,880.

EXAMPLE 11

The procedure of Example 8 is followed, but a suspension of 3,3-dimethyl-2-oxobutyl 5-chloropyrid-2-yldithiocarbamate (18.1 g) in acetonitrile (360 cc) and a solution of potassium borohydride (5.4 g) in distilled water (90 cc) are used as the starting materials at a maximum of 40° C. The reaction is allowed to proceed for 3 hours at between 35° and 40° C. After recrystallisation of the product from acetonitrile (160 cc), 3,3-dimethyl-2-hydroxybutyl 5-chloropyrid-2-yldithiocarbamate (15.3 g), which melts at 149° C., is obtained.

3,3-Dimethyl-2-oxobutyl 5-chloropyrid-2-yldithiocarbamate can be prepared in the following manner: Triethylammonium 5-chloropyrid-2-yldithiocarbamate (230 g) and 1-bromo-3,3-dimethylbutan-2-one (135 g) are reacted in anhydrous acetonitrile (2,000 cc) at 20° C. The reaction is allowed to proceed for 2 hours at 20° C. After recrystallisation from ethanol (1,700 cc), 3,3-dimethyl-2-oxobutyl 5-chloropyrid-2-yldithiocarbamate (142.1 g), which melts at 139° C., is obtained.

EXAMPLE 12

The procedure of Example 8 is followed, but a suspension of phenacyl 5-chloropyrid-2-yldithiocarbamate (23.1 g) in acetonitrile (240 cc) and a solution of potassium borohydride (3.9 g) in distilled water (60 cc) are used as the starting materials at between 20° and 28° C. The reaction is allowed to proceed for 45 minutes at 25° C. After adding a 3 N aqueous solution of hydrochloric acid (23.8 cc), filtering off the crystals, washing them with ice-cooled acetonitrile (15 cc) and then three times with distilled water (180 cc in total) and drying them under reduced pressure (0.2 mm Hg) at 40° C., 2-hydroxy-2-phenylethyl 5-chloropyrid-2-yldithiocarbamate (13.6 g), which melts at 116° C., is obtained.

Phenacyl 5-chloropyrid-2-yldithiocarbamate can be prepared in the following manner: Triethylammonium 5-chloropyrid-2-yldithiocarbamate (38.3 g) and phenacyl bromide (24.9 g) are reacted in anhydrous acetonitrile (250 cc) at between 20° and 25° C. The reaction is allowed to proceed for 30 minutes at 20° C. After recrystallisation from acetonitrile (200 cc), phenacyl 5-chloropyrid-2-yldithiocarbamate (33.9 g), which melts at 145° C., is obtained.

When the product is examined by I.R. spectroscopy in chloroform solution, about 95% of 3-(5-chloropyrid-2-yl)-4-hydroxy-4-phenylthiazolidine-2-thione is observed (reduction in the carbonyl band at 1,690 cm$^{-1}$). This form is not detectable when the product is examined between plates in petroleum jelly.

EXAMPLE 13

The procedure of Example 4 is followed, but a suspension of [2-(4-fluorophenyl)-2-oxo]-ethyl 5-chloropyrid-2-yldithiocarbamate (17.1 g) in acetonitrile (160 cc) and a solution of potassium borohydride (2.7 g) in distilled water (40 cc) are used as the starting materials at a maximum of 25° C. The reaction is allowed to proceed for 1 hour at between 20° and 25° C. After recrystallisation from acetonitrile (70 cc), 2-(4-fluorophenyl)-2- hydroxyethyl 5-chloropyrid-2-yldithiocarbamate (13.3 g), which melts at 120° C., is obtained.

[2-(4-Fluorophenyl)-2-oxo]-ethyl 5-chloropyrid-2-yldithiocarbamate can be prepared in the following manner: A solution of 2-chloro-1-(4-fluorophenyl)-ethan-1-one (34.5 g) in anhydrous acetonitrile (100 cc) is added, at between 20° and 25° C., to a suspension of triethylammonium 5-chloropyrid-2-yldithiocarbamate (61.1 g) in anhydrous acetonitrile (600 cc). The reaction is allowed to proceed for 1 hour at 20° C. The solid which crystallises is filtered off, washed 3 times with distilled water (600 cc in total) and 3 times with ethanol (450 cc in total) and then dried in the atmosphere for 16 hours. The resulting product (47.4 g) is purified by recrystallisation from boiling acetonitrile (330 cc). After filtering the boiling solution and then cooling for 3 hours at 2° C., the crystals which have appeared are filtered off, washed 3 times with ice-cooled acetonitrile (90 cc in total) and dried under reduced pressure (0.1 mm Hg) at 45° C. [2-(4-Fluorophenyl)-2-oxo]-ethyl 5-chloropyrid-2-yldithiocarbamate (32.3 g), which melts at 146° C., is thus obtained.

When the product is examined by I.R. spectroscopy in chloroform solution, a very significant reduction in the intensity of the carbonyl band at 1,690 cm$^{-1}$ is observed, which corresponds to the presence of about 70% of 3-(5-chloropyrid-2-yl)-4-(4-fluorophenyl)-thiazolidine-2-thione.

2-Chloro-1-(4-fluorophenyl)-ethan-1-one (m.p.=50° C.) is prepared in accordance with the method described by R. M. HANN and J. P. WETHERILL, J. Wash. Acad. Sci., 24 526 (1934).

EXAMPLE 14

A 5 N aqueous solution of sodium hydroxide (10.0 cc) is added, at a maximum of 20° C., to a suspension of 2-(3-methylphenyl)-2-oxoethyl 5-chloropyrid-2-yldithiocarbamate (16.8 g) in methanol (150 cc), and a solution of potassium borohydride (2.7 g) in distilled water (30 cc) is then added at a maximum of 20° C. The reaction is allowed to proceed for 1 hour at 20° C. A 5 N aqueous solution of hydrochloric acid (20 cc) is added at a maximum of 20° C. The reaction mixture is diluted by adding distilled water (250 cc) and the solid which precipitates is then filtered off, washed 4 times with distilled water (600 cc in total) and dried for 16 hours in the atmosphere.

The resulting product (17.0 g) is purified by recrystallisation from boiling acetonitrile (100 cc) in the presence of decolourising charcoal (0.6 g). After filtering the boiling solution and then cooling for 3 hours at 2° C., the crystals which have appeared are filtered off, washed 3 times with ice-cooled acetonitrile (90 cc in total) and dried under reduced pressure (0.1 mm Hg) at 45° C. 2-Hydroxy-2-(3-methylphenyl)-ethyl 5-chloro-pyrid-2-yldithiocarbamate (15.0 g), which melts at 122° C., is thus obtained.

2-(3-Methylphenyl)-2-oxoethyl 5-chloropyrid-2-yldithiocarbamate can be prepared in the following manner: A solution of 2-bromo-1-(3-methylphenyl)-ethan-1-one (31.9 g) in anhydrous acetonitrile (100 cc) is added, at 20° C., to a suspension of triethylammonium 5-chloro-pyrid-2-yldithiocarbamate (45.7 g) in anhydrous acetonitrile (1,000 cc). The reaction is allowed to proceed for 3 hours at 20° C. The acetonitrile is evaporated off under reduced pressure (20 mm Hg) at 45° C. The residual solid is taken up in distilled water (250 cc) and then, after filtration, washed 3 times with distilled water (600 cc in total) and twice with ice-cooled ethanol (300 cc in total). After drying in the atmosphere for 16 hours, yellow crystals (35.7 g), which melt at 128° C., are obtained and these are purified by recrystallisation from boiling acetonitrile (650 cc); after filtering the boiling solution and then cooling for 2 hours at 2° C., the crystals which have appeared are filtered off, washed twice with ice-cooled acetonitrile (200 cc in total) and dried under reduced pressure (0.1 mm Hg) at 45° C. 2-(3-Methylphenyl)-2-oxoethyl 5-chloropyrid-2-yldithiocarbamate (13.4 g), which melts at 126° C., is thus obtained.

When the product is examined by I.R. spectroscopy in chloroform solution, a very significant reduction in the intensity of the carbonyl band at 1,660 cm$^{-1}$ is observed, which corresponds to the presence of about 90% of 3-(5-chloropyrid-2-yl)-4-hydroxy-4-(3-methylphenyl)-thiazolidine-2-thione.

Triethylammonium 5-chloropyrid-2-yldithiocarbamate (m.p.=130° C.) is prepared in accordance with the method described by D. B. CAPPS in U.S. Pat. No. 3,726,880.

2-Bromo-1-(3-methylphenyl)-ethan-1-one (b.p.$_{94}$=105° C.) is prepared in accordance with the method described by R. M. LAIRD and R. E. PARKER, J. Amer. Chem. Soc., 83, 4,277 (1961).

EXAMPLE 15

The procedure of Example 3 is followed, but a suspension of 4-hydroxy-3-(pyrid-2-yl)-perhydro-1, 3-thiazine-2-thione (2.26 g) in methanol (32 cc) and a solution of potassium borohydride (0.54 g) in distilled water (8 cc) are used as the starting materials at a maximum of 40° C. The reaction is allowed to proceed for 30 minutes at between 30° and 40° C. After recrystallisation from acetonitrile (8 cc), 3-hydroxypropyl pyrid-2-yldithiocarbamate (1.35 g), which melts at 93° C., is obtained.

4-Hydroxy-3-(pyrid-2-yl)-perhydro-1,3-thiazine-2-thione can be prepared in the following manner: A solution of acrolein (19.5 g) in anhydrous acetonitrile (45 cc) is added, at a maximum of 10° C., to a suspension of triethylammonium pyrid-2-yldithiocarbamate (90.0 g) in anhydrous acetonitrile (450 cc). The reaction is allowed to proceed for 1 hour at a maximum of 10° C. A 2.3 N aqueous solution of hydrochloric acid (144 cc) is added at a maximum of 10° C. The crystals which have appeared are filtered off, washed twice with acetonitrile (50 cc in total) and three times with distilled water (120 cc in total) and dried under reduced pressure (20 mm Hg) at 20° C. A first fraction of product (17.8 g), which melts at 115° C., is obtained. The filtrate is evaporated to dryness under reduced pressure (20 mm Hg) at 45° C. The resulting residue is dissolved in methylene chloride (600 cc). The organic solution is washed four times with distilled water (600 cc in total), dried over sodium sulphate and evaporated. The resulting product (50.0 g) is purified by recrystallisation from ethanol (150 cc). A second fraction of product (13.3 g), which melts at 113°–115° C., is obtained. The two fractions are combined and dissolved in boiling methylene chloride (170 cc); ethyl ether (170 cc) is added. After 3 hours at 2° C., the crystals which have appeared are filtered off, washed with a mixture of methylene chloride (15 cc) and ethyl ether (15 cc) and then twice with ethyl ether (60 cc) and dried under reduced pressure (0.2 mm Hg) at 50° C. 4-Hydroxy-3-(pyrid-2-yl)-perhydro-1,3-thiazine-2-thione (23.0 g), which melts at 120° C., is thus obtained.

When the product is examined by I.R. spectroscopy in chloroform solution, a band at 1,725 cm$^{-1}$ is observed, which may correspond to a maximum of 5% of 2-formylethyl pyrid-2-yldithiocarbamate. This band is not observed when the product is examined between plates in petroleum jelly.

Triethylammonium pyrid-2-yldithiocarbamate (m.p.=95° C.) is prepared in accordance with the method described by E. B. KNOTT, J. Chem. Soc., 1,644–9 (1956).

EXAMPLE 16

The procedure of Example 3 is followed, but a solution of 3-oxobutyl pyrid-2-yldithiocarbamate (12.0 g) in methanol (160 cc) and a solution of potassium borohydride (2.7 g) in distilled water (40 cc) are used as the starting materials at a maximum of 33° C. The reaction is allowed to proceed for 1 hour at 20°–33° C. After recrystallisation from ethyl acetate (60 cc), 3-hydroxybutyl pyrid-2-yldithiocarbamate (8.3 g), which melts at 104° C., is obtained.

3-Oxobutyl pyrid-2-yldithiocarbamate can be prepared in the following manner: A solution of but-3-en-2-one (11.6 g) in anhydrous acetonitrile (15 cc) is added, at a maximum of 5° C., to a suspension of triethylammonium pyrid-2-yldithiocarbamate (45.0 g) in anhydrous acetonitrile (280 cc). The reaction is allowed to proceed for 2 hours at a maximum of 2° C. A 3.5 N solution of hydrogen chloride in ethyl ether (47.5 cc) is added at a maximum of 0° C. The triethylamine hydrochloride is filtered off and washed twice with a mixture of acetonitrile (40 cc in total) and ethyl ether (140 cc in total). The solvents are evaporated off under reduced pressure (20 mm Hg) at 45° C. The residue is treated with ethyl ether (600 cc). The ether solution is washed twice with distilled water (240 cc in total), dried over sodium sulphate and evaporated. The resulting residue (30.2 g) is dissolved in methylene chloride (120 cc), silica (0.2–0.5 mm, 25.0 g) is added and the solvent is then evaporated off. The silica impregnated with the product is introduced into a column of diameter 4 cm, containing silica (0.2–0.5 mm, 300 g). Elution is carried out successively with a mixture of cyclohexane (1,600 cc) and ethyl acetate (400 cc) and then with a mixture of cyclohexane (375 cc) and ethyl acetate (125 cc), these eluates being discarded. Elution is continued with a mixture of cyclohexane (1,800 cc) and ethyl acetate (600 cc). This eluate is collected and then evaporated to dryness under reduced pressure (20 mm Hg) at 45° C. The resulting crystals (24.5 g; m.p. about 65° C.) are treated with a mixture of isopropyl ether (60 cc) and ethyl ether (60 cc). The crystals are filtered off, washed successively with a mixture of isopropyl ether (25 cc) and ethyl ether (25 cc) and then twice with isopropyl ether (50 cc) and dried under reduced pressure (20 mm Hg) at 40° C. 3-Oxobutyl pyrid-2-yldithiocarbamate (21.2 g) (structure determined by I.R. spectroscopy in petroleum jelly), which melts at 74° C., is thus obtained.

EXAMPLE 17

The procedure of Example 3 is followed, but a suspension of 4,4-dimethyl-3-oxopentyl pyrid-2-yldithiocarbamate (14.1 g) in methanol (160 cc) and a solution of potassium borohydride (5.4 g) in distilled water (40 cc) are used as the starting materials at a maximum of 30° C. The reaction is allowed to proceed for 2 hours at between 20° and 30° C. After recrystallisation from isopropyl ether (65 cc), 3-hydroxy-4,4-dimethylpentyl pyrid-2-yldithiocarbamate (10.3 g), which melts at 94° C., is obtained.

4,4-Dimethyl-3-oxopentyl pyrid-2-yldithiocarbamate can be prepared in the following manner: A solution of 2,2-dimethylpent-4-en-3-one (22.5 g) in anhydrous acetonitrile (50 cc) is added, at a maximum of 5° C., to a suspension of triethylammonium pyrid-2-yl-dithiocarbamate (54.2 g) in anhydrous acetonitrile (150 cc). The reaction is allowed to proceed for 2 hours at between 5° and 20° C. The acetonitrile is evaporated off under reduced pressure (20 mm Hg) at 45° C. The resulting residue is dissolved in methylene chloride (600 cc). The organic solution is washed four times with distilled water (600 cc), dried over sodium sulphate and evaporated. The resulting product (58.0 g) is dissolved in a mixture of chloroform (360 cc) and ethyl acetate (40 cc). The solution is chromatographed on a column of diameter 6 cm containing silica (0.063–0.2 mm) (600 g). Elution is carried out with a mixture of chloroform (720 cc) and ethyl acetate (80 cc), this eluate being discarded, and then with a mixture of chloroform (3,000 cc) and ethyl acetate (350 cc), this eluate being collected and evaporated to dryness under reduced pressure (20 mm Hg) at 45° C. The resulting product (42.0 g) is purified by recrystallisation from isopropyl ether (200 cc). 4,4-Dimethyl-3-oxopentyl pyrid-2-yldithiocarbamate (36.0 g) (structure determined by I.R. spectroscopy in petroleum jelly), which melts at 95° C., is obtained.

2,2-Dimethylpent-4-en-3-one (b.p.=65°–67° C./0.5 mm Hg) is prepared in accordance with the method described by C. W. SPANGLER, J. Org. Chem., 38, 3,483 (1973).

EXAMPLE 18

The procedure of Example 8 is followed, but a suspension of 3-(5-chloropyrid-2-yl)-4-hydroxyperhydro-1,3-thiazine-2-thione (130.0 g) in acetonitrile (200 cc) and a solution of potassium borohydride (2.7 g) in distilled water (50 cc) are used as the starting materials at between 15° and 20° C. The reaction is allowed to proceed for 20 minutes at 20° C. After recrystallisation from isopropyl ether (165 cc), 3-hydroxypropyl 5-chloropyrid-2-yldithiocarbamate (9.25 g), which melts at 83° C., is obtained.

3-(5-Chloropyrid-2-yl)-4-hydroxy-perhydro-1,3-thiazine-2-thione can be prepared in the following manner: A solution of acrolein (17.6 g) in anhydrous acetonitrile (45 cc) is added, at a maximum of 5° C., to a suspension of triethylammonium 5-chloropyrid-2-yldithiocarbamate (91.5 g) in anhydrous acetonitrile (450 cc). The reaction is allowed to proceed for 90 minutes at a maximum of 5° C. The crystals which have appeared are filtered off, washed with ice-cooled acetonitrile (50 cc) and then four times with distilled water (480 cc in total) and dried in air. The resulting product (38.8 g; m.p.=136°–137° C.) is purified by recrystallisation from acetonitrile (240 cc). 3-(5-Chloropyrid-2-yl)-4-hydroxy-perhydro-1, 3-thiazine-2-thione (33.2 g), which melts at 141° C., is obtained.

When the product is examined by I.R. spectroscopy in chloroform solution, a band at 1,720 cm$^{-1}$ is observed, which may correspond to a maximum of 5% of 2-formylethyl 5-chloropyrid-2-yldithiocarbamate. This band is not observed when the product is examined between plates in petroleum jelly.

Triethylammonium 5-chloropyrid-2-yldithiocarbamate (m.p.=130° C.) is prepared in accordance with the method described by D. B. CAPPS in U.S. Pat. No. 3,726,880.

EXAMPLE 19

The procedure of Example 3 is followed, but a suspension of 3-oxobutyl 5-chloropyrid-2-yldithiocarbamate (17.5 g) in methanol (220 cc) and a solution of potassium borohydride (3.44 g) in distilled water (55 cc) are used as the starting materials at a maximum of 30° C. The reaction is allowed to proceed for 1 hour at between 20° and 30° C. The resulting product (14.2 g; m.p.=115° C.) is dissolved in chloroform (500 cc). The solution is chromatographed on silica (0.2–0.5 mm) (140 g) contained in a column of diameter 3.4 cm. Elution is carried out with chloroform (1,500 cc), this eluate being discarded, and then with chloroform (4 liters). The eluate which is collected is evaporated to dryness under reduced pressure (20 mm Hg) at 45° C. The chromatographed product (11.4 g) is recrystallised from acetonitrile (85 cc). 3-Hydroxybutyl 5-chloropyrid-2-yldithiocarbamate (11.0 g), which melts at 122° C., is obtained.

3-Oxobutyl 5-chloropyrid-2-yldithiocarbamate can be prepared in the following manner: A solution of but-3-en-2-one (25.6 g) in anhydrous chloroform (90 cc) is added, at a maximum of 5° C., to a suspension of triethylammonium 5-chloropyrid-2-yldithiocarbamate (110.0 g) in anhydrous chloroform (540 cc). The reaction is allowed to proceed for 1 hour at a maximum of 5° C. A 3.7 N solution of hydrogen chloride in ethyl ether (97 cc) is added at a maximum of 0° C. and the resulting mixture is diluted with chloroform (500 cc). The chloroform solution is washed 3 times with distilled water (450 cc in total), dried over sodium sulphate and evaporated. The resulting residue (95.0 g) is dissolved in methylene chloride (300 cc), silica (0.2–0.5 mm, 60.0 g) is added and the solvent is evaporated off. The silica impregnated with the product is introduced into a column of diameter 7.5 cm, containing silica (0.2–0.5 mm, 900 g). Elution is carried out first with a mixture of cyclohexane (6 liters) and ethyl acetate (1 liter), this eluate being discarded, and then with a mixture of cyclohexane (11.4 liters) and ethyl acetate (6.6 liters), this eluate being collected and evaporated to dryness under reduced pressure (20 mm Hg) at 45° C. The resulting product (65.2 g: m.p.=116° C.) is purified by two recrystallisations, successively from acetonitrile (210 cc) and then from a mixture of chloroform (250 cc) and ethyl ether (250 cc). 3-Oxobutyl 5-chloropyrid-2-yldithiocarbamate (47.5 g) (structure determined by I.R. spectroscopy in petroleum jelly), which melts at 120° C., is obtained.

EXAMPLE 20

The procedure of Example 3 is followed, but a suspension of 4,4-dimethyl-3-oxopentyl 5-chloropyrid-2-yldithiocarbamate (15.8 g) in methanol (160 cc) and a solution of potassium borohydride (2.75 g) in distilled water (40 cc) are used as the starting materials at a maximum of 30° C. The reaction is allowed to proceed for 3 hours at between 20° and 30° C. After recrystallisation from acetonitrile (60 cc), 3-hydroxy-4,4-dimethylpentyl 5-chloropyrid-2-yldithiocarbamate (12.4 g), which melts at 120° C., is obtained.

4,4-Dimethyl-3-oxopentyl 5-chloropyrid-2-yldithiocarbamate can be prepared in accordance with one or other of the following methods:

(A) A solution of 2,2-dimethylpent-4-en-3-one (30.0 g) in anhydrous acetonitrile (60 cc) is added, at a maximum of 5° C., to a suspension of triethylammonium 5-chloropyrid-2-yldithiocarbamate (82.0 g) in anhydrous acetonitrile (400 cc). The reaction is allowed to proceed for 3 hours at between 5° and 20° C. The crystals which have appeared are filtered off and the filtrate is evaporated under reduced pressure (20 mm Hg) at 45° C. The resulting residue and the crystals which have been separated beforehand are dissolved in methylene chloride (750 cc). The organic solution is washed 4 times with distilled water (600 cc in total), dried over sodium sulphate and evaporated. The resulting product (98.0 g) is dissolved in chloroform (400 cc). The solution is chromatographed on a column of diameter 6.8 cm, containing silica (0.063–0.2 mm, 800 g). Elution is carried out first with chloroform (2.6 liters), this eluate being discarded, and then with chloroform (7.2 liters), this eluate being collected and evaporated to dryness. The resulting product (85.0 g) is purified by recrystallisation from acetonitrile (350 cc). 4,4-Dimethyl-3-oxopentyl 5-chloropyrid-2-yldithiocarbamate (70.0 g) (structure determined by I.R. spectroscopy in petroleum jelly), which melts at 111° C., is obtained.

(B) (4,4-Dimethyl-3-oxopentyl)-trimethylammonium iodide (6.0 g) is added, at 20° C., to a suspension of triethylammonium 5-chloropyrid-2-yldithiocarbamate (6.1 g) in anhydrous acetonitrile (25 cc). The reaction is allowed to proceed for 6 hours at 20° C. Distilled water (25 cc) is added. The crystals which have appeared are filtered off, washed three times with distilled water (30 cc in total) and dried in air at 20° C. The resulting product (5.1 g; m.p.=110° C.) is recrystallised from acetonitrile (15 cc). 4,4-Dimethyl-3-oxopentyl 5-chloropyrid-2-yldithiocarbamate (3.8 g), which melts at 111° C., is obtained.

(4,4-Dimethyl-3-oxopentyl)-trimethylammonium iodide (instantaneous m.p.=260° C.) is prepared in accordance with the method described by A. N. KOST and V. V. ERSHOV, Zhur. Obshchei Khim., 27, 1,722–26(1957).

EXAMPLE 21

The procedure of Example 3 is followed, but a suspension of 3-oxo-3-phenylpropyl 5-chloropyrid-2-yldithiocarbamate (28.0 g) in methanol (840 cc) and a solution of potassium borohydride (9.0 g) in distilled water (120 cc) are used as the starting materials at a maximum of 30° C. The reaction is allowed to proceed for 20 hours at between 20° and 25° C. Unreacted starting material (5.5 g) is filtered off from the reaction mixture. The filtrate is evaporated to dryness. The residue (20.0 g) is dissolved in chloroform (200 cc). The solution is chromatographed on silica (0.063–0.2 mm, 400 g) contained in a column of diameter 5 cm. Elution is carried out with chloroform (2 liters), this eluate being discarded, and then with chloroform (4.5 liters). The eluate which is collected is evaporated to dryness under reduced pressure (20 mm Hg) at 45° C. The chromatographed product (14.4 g) is recrystallised from acetonitrile (40 cc). 3-Hydroxy-3-phenylpropyl 5-chloropyrid-2-yldithiocarbamate (9.8 g), which melts at 91° C., is obtained.

3-Oxo-3-phenylpropyl 5-chloropyrid-2-yldithiocarbamate can be prepared in the following manner: The procedure of Example 17 is followed, but a suspension of triethylammonium 5-chloropyrid-2-yldithiocarbamate (65.0 g) in a mixture of acetonitrile (225 cc) and distilled water (25 cc), and a solution of 1-phenylprop-2-en-1-one (26.5 g) in acetonitrile (50 cc), are used as the starting materials at a maximum of 5° C. The reaction is allowed to proceed for 3 hours at between 5° and 20° C. The crystals which have appeared are filtered off, washed 3 times with ice-cooled acetonitrile (60 cc in total) and then with isopropyl ether (50 cc) and dried under reduced pressure (20 mm Hg) at 40° C. 3-Oxo-3-phenylpropyl 5-chloropyrid-2-yldithiocarbamate (57.0 g), which melts at 159° C., is obtained.

1-Phenylprop-2-en-1-one (b.p. = 117°-118° C./20 mm Hg) is prepared in accordance with the method described by F. F. BLICKE and J. H. BURCKHALTER, J. Amer. Chem. Soc., 64, 454 (1942).

EXAMPLE 22

The procedure of Example 1 is followed, but a suspension of 3-(4-fluorophenyl)-3-oxopropyl 5-chloropyrid-2-yldithiocarbamate (25.0 g) in acetonitrile (225 cc) and a solution of potassium borohydride (5.6 g) in distilled water (56 cc) are used as the starting materials at a maximum of 25° C. The reaction is allowed to proceed for 1 hour at between 20° and 25° C. The residual oil thus obtained (20.2 g) is dissolved in a mixture (100 cc) of chloroform (80 cc) and ethyl acetate (20 cc) and the solution is chromatographed on a column of diameter 4 cm, containing silica (0.063–0.2 mm, 450 g). Elution is carried out first with a mixture of chloroform (800 cc) and ethyl acetate (200 cc), this eluate being discarded, and then with a mixture (2,500 cc) of chloroform (2,000 cc) and ethyl acetate (500 cc), this eluate being evaporated under reduced pressure (20 mm Hg) at 50° C. The resulting product (16.5 g) is recrystallised from boiling isopropyl ether (80 cc). After filtering the boiling solution and then cooling for 2 hours at 2° C., the crystals which have appeared are filtered off, washed 4 times with ice-cooled isopropyl ether (20 cc in total), and dried under reduced pressure (0.1 mm Hg) at 45° C. 3-(4-Fluorophenyl)-3-hydroxypropyl 5-chloropyrid-2-yldithiocarbamate (12.1 g), which melts at 86° C., is thus obtained.

3-(4-Fluorophenyl)-3-oxopropyl 5-chloropyrid-2-yldithiocarbamate can be prepared as described in Example 3, using a suspension of triethylammonium 5-chloropyrid-2-yldithiocarbamate (54.0 g) in acetonitrile (450 cc) and 3-(4-fluorophenyl)-3-oxo-N,N,N-trimethylpropan-1-aminium iodide (58.4 g) as the starting materials. The reaction is allowed to proceed for 5 hours at 20° C. After recrystallisation from boiling acetonitrile (160 cc), 3-(4-fluorophenyl)-3-oxopropyl 5-chloropyrid-2-yldithiocarbamate (13.8 g), which melts at 144° C., is obtained.

3-(4-Fluorophenyl)-3-oxo-N,N,N-trimethylpropan-1-aminium iodide can be prepared in accordance with the following procedure: Dimethylamine hydrochloride (32.6 g), a 12 N aqueous solution of hydrochloric acid (1 cc) and polyoxymethylene (12.0 g) are added to a solution of 1-(4-fluorophenyl)-ethanone (56.0 g) in ethanol (200 cc). After heating under reflux for 3 hours, more polyoxymethylene (6.0 g) is added and the mixture is heated under reflux for a further 16 hours. The reaction mixture is cooled to 20° C. and diethyl ether (300 cc) is then added. The solid which precipitates is filtered off, washed 3 times with diethyl ether (300 cc in total) and dried under reduced pressure (20 mm Hg) at 25° C. for 16 hours. 2-Dimethylamino-1-(4-fluorophenyl)-ethan-1-one hydrochloride (65.0 g), which melts at 180° C., is thus obtained and this is dissolved in distilled water (60 cc). Diethyl ether (1,100 cc) and a 10 N aqueous solution of sodium hydroxide (30 cc) are added to the solution thus obtained, the mixture is stirred for 2 minutes and the organic phase is decanted. The aqueous phase is re-extracted twice with diethyl ether (300 cc in total). The ether extracts are combined, dried over sodium sulphate and evaporated under reduced pressure (20 mm Hg) at 40° C. Methyl iodide (42.5 g) is added, at between 20° and a maximum of 50° C., to a solution of the residual oil (52.2 g) in anhydrous acetonitrile (250 cc). The reaction is allowed to proceed for 2 hours at 20° C. and diethyl ether (300 cc) is then added. The solid which precipitates is filtered off, washed 3 times with diethyl ether (300 cc in total), and dried under reduced pressure (20 mm Hg) at 25° C. for 16 hours. 3-(4-Fluorophenyl)-3-oxo-N,N,N-trimethylpropan-1-aminium iodide (65.5 g), which melts at 230° C., is thus obtained.

EXAMPLE 23

The procedure of Example 1 is followed, but a suspension of 3-(3-methylphenyl)-3-oxopropyl 5-chloropyrid-2-yldithiocarbamate (20.4 g) in acetonitrile (280 cc) and a solution of potassium borohydride (4.7 g) in distilled water (70 cc) are used as the starting materials at a maximum of 30° C. The reaction is allowed to proceed for 30 minutes at between 25° and 30° C. After recrystallisation from isopropyl ether (100 cc), 3-hydroxy-3-(3-methylphenyl)-propyl 5-chloropyrid-2-yldithiocarbamate (10.0 g), which melts at 74° C., is obtained.

3-(3-Methylphenyl)-3-oxopropyl 5-chloropyrid-2-yldithiocarbamate can be prepared in the following manner: 3-(3-Methylphenyl)-3-oxo-N,N,N-trimethylpropan-1-aminium iodide (52.0 g) is added in small amounts, at between 18° and 20° C., to a suspension of triethylammonium 5-chloropyrid-2-yldithiocarbamate (47.5 g) in anhydrous acetonitrile (400 cc). The reaction is allowed to proceed for 6 hours at 20° C. Distilled water (400 cc) is added to the reaction mixture, and the solid which precipitates is filtered off, washed 4 times with distilled water (800 cc in total) and dried for 16 hours in the atmosphere. The resulting product (37.5 g) is dissolved in chloroform (300 cc), silica (0.2–0.5 mm, 60.0 g) is added and the solvent is then evaporated off. The silica impregnated with the product is deposited on a column of diameter 4 cm, containing silica (0.2–0.5 mm, 700 g). Elution is carried out first with chloroform (1.5 liters), this eluate being discarded, and then with chloroform (3 liters), this eluate being evaporated under reduced pressure (20 mm Hg) at 50° C. The resulting product (31.3 g) is recrystallised from boiling acetonitrile (100 cc). After filtering the boiling solution and then cooling for 2 hours at 2° C., the crystals which have appeared are filtered off, washed twice with ice-cooled acetonitrile (50 cc in total), and dried under reduced pressure (0.1 mm Hg) at 45° C. 3-(3-Methylphenyl)-3-oxopropyl 5-chloropyrid-2-yldithiocarbamate (30.4 g), which melts at 153° C., is thus obtained.

3-(3-Methylphenyl)-3-oxo-N,N,N-trimethylpropan-1-aminium iodide (m.p. = 240° C.) is prepared analogously to the method of E. D. THORSETT and F. R. STERMITZ, Syn. Commun., 2 (6) 375-81 (1972), for the preparation of 3-(2-methylphenyl)-3-oxo-N,N,N-trimethylpropan-1-aminium iodide.

EXAMPLE 24

A solution of potassium borohydride (21.5 g) in distilled water (150 cc) is added, at a maximum of 30° C., to a suspension of 3-(pyrid-2-yl)-rhodanine (42.0 g) in methanol (650 cc). The reaction is allowed to proceed for 1 hour at between 20° and 30° C. The methanol is evaporated off under reduced pressure (20 mm Hg) at 45° C. The residue is treated with distilled water (300 cc) and then with a 5 N aqueous solution of hydrochloric acid (80 cc). The oil which has been salted out is extracted 3 times with methylene chloride (400 cc in total). The organic solution is washed with distilled water (100 cc), dried over sodium sulphate and evaporated. The resulting oily residue (27.0 g) is dissolved in methylene chloride (60 cc), and the solution obtained is chromatographed on silica (0.063–0.2 mm, 400 g) contained in a column of diameter 5 cm. Elution is carried out first with methylene chloride (5 liters), this eluate being discarded, and then with methylene chloride (10 liters), this eluate being evaporated. After recrystallisation of the resulting product (20.0 g) from a mixture of acetonitrile (100 cc) and isopropyl ether (100 cc), 2-hydroxyethyl pyrid-2-yldithiocarbamate (12.2 g), which melts at 88° C., is obtained.

3-(Pyrid-2-yl)-rhodanine (m.p.=98° C.) is prepared in accordance with the method described by E. B. KNOTT, J. Chem. Soc., 1, 648 (1956).

EXAMPLE 25

The procedure of Example 24 is followed, but a suspension of 3-(pyrid-2-yl)-2-thioxo-perhydro-1,3-thiazin-4-one (22.4 g) in methanol (300 cc) and a solution of potassium borohydride (10.8 g) in distilled water (75 cc) are used as the starting materials at a maximum of 40° C. The reaction is allowed to proceed for 1 hour at between 25° and 40° C. The reaction mixture is evaporated to dryness and the residue (21.5 g) is dissolved in a mixture of ethyl acetate (70 cc) and cyclohexane (30 cc). The solution is chromatographed on silica (0.2–0.5 mm) (300 g) distributed in a column of diameter 4.5 cm. Elution is carried out with a mixture of ethyl acetate (520 cc) and cyclohexane (180 cc), this eluate being discarded, and then with a mixture of ethyl acetate (1,660 cc) and cyclohexane (540 cc). The eluate which is collected is evaporated to dryness under reduced pressure (20 mm Hg) at 45° C. 3-Hydroxypropyl pyrid-2-yldithiocarbamate (12.2 g), which melts at 93° C., is obtained.

3-(Pyrid-2-yl)-2-thioxo-perhydro-1,3-thiazin-4-one (m.p.=157° C.) is prepared in accordance with the method described in U.S. Pat. No. 3,732,216.

EXAMPLE 26

A solution of 2-hydroxymethyloxirane (8.25 g) in anhydrous acetonitrile (30 cc) is added, at 20° C., to a suspension of triethylammonium pyrid-2-yldithiocarbamate (27.1 g) in anhydrous acetonitrile (250 cc). The reaction is allowed to proceed for 16 hours at 20° C. The acetonitrile is evaporated off under reduced pressure (20 mm Hg) at 45° C. The residual oil thus obtained (24.3 g) is dissolved in chloroform (200 cc) and the solution is chromatographed on a column of diameter 5.5 cm, containing silica (0.2–0.5 mm, 500 g). Elution is carried out first with chloroform (3.5 liters), this eluate being discarded, and then with chloroform (1.3 liters), this eluate being evaporated under reduced pressure (20 mm Hg) at 45° C. The residual solid is taken up in chloroform (100 cc), filtered off, washed 3 times with chloroform (30 cc in total), and dried under reduced pressure (0.1 mm Hg) at 45° C.

2,3-Dihydroxypropyl pyrid-2-yldithiocarbamate (14.0 g), which melts at 98° C., is thus obtained and is similar in all respects to the product obtained as in Example 4.

The present invention includes within its scope pharmaceutical compositions (for use in human or animal medicine) which comprise, as active ingredient, at least one compound of the formula (I), optionally as a non-toxic salt, in association with one or more compatible and pharmaceutically acceptable diluents or adjuvants and, optionally, with other compatible and physiologically active products. These compositions may be in a form suitable for oral, parenteral or rectal administration.

Solid compositions for oral administration include tablets, pills, powders, sugar-coated pills and granules. In these compositions, the active compound is mixed with one or more inert diluents such as sucrose, lactose or starch. These compositions can also comprise substances other than diluents, e.g. a lubricant such as magnesium stearate.

Liquid compositions for oral administration include pharmaceutically acceptable emulsions, solutions, suspensions, syrups, and elixirs containing inert diluents commonly used in the art such as water or paraffin oil. These compositions can also comprise substances other than diluents, e.g. wetting, emulsifying and suspending agents, sweeteners, flavourings and aromatizing agents.

The compositions of the invention for oral administration also include capsules of absorbable material such as gelatin containing the active substance with or without the addition of diluents or excipients.

Compositions for parenteral administration include sterile aqueous or non-aqueous suspensions, emulsions or sterile solutions. Propylene glycol, polyethylene glycol, vegetable oils, in particular olive oil, or injectable organic esters, such as ethyl oleate, can be employed as non-aqueous solvents or vehicles. These compositions can also contain adjuvants, such as preservatives, wetting agents, emulsifiers, and dispersing agents. Sterilization can be carried out in several ways, e.g. using a bacteriological filter, by incorporating sterilising agents into the composition, by irradiation, or by heating. The compositions can also be prepared in the form of sterile compositions which can be dissolved, at the time of use, in sterile water or in any other injectable sterile medium.

The compositions for rectal administration are suppositories which can contain, in addition to the active product, excipients such as cacao butter or suppository wax.

In these various compositions, the active ingredient, when it is not dissolved, is advantageously in micronised form.

The compounds of the invention are useful as anthelmintics.

In veterinary medicine, they can be used in the treatment of helminthiases caused by nematodes in cattle, sheep, horses and goats, at doses of between 5 and 50 mg/kg, administered orally, for treatments lasting from 1 to 3 days, or between 2.5 and 25 mg/kg of body weight of the animal, over prolonged periods, as well as for the removal of gastro-intestinal strongyles in sheep and intestinal nematodes in dogs.

In human medicine, the compounds of the invention can be used for removing anguillulae, ascarides and ankylostomes, in doses of between 5 and 50 mg/kg, administered orally, for treatments lasting from 1 to 3 days.

The compositions according to the invention can also be particularly useful in therapy in the treatment and prevention of human filarioses, namely cutaneo-dermic filarioses (onchocercosis, loasis and dracunculosis) and lymphatic filarioses (wuchereriasis and brugiasis).

In human therapy, the doses depend on the desired effect and the duration of the treatment; for an adult, they are generally between 10 and 50 mg/kg per day, administered orally, and between 5 and 15 mg/kg per day, administered intramuscularly, for treatments lasting from 1 to 30 days.

In general, the physician or veterinary surgeon will decide the posology which he considers to be most appropriate as a function of the age, the weight and all the other factors intrinsic to the subject to be treated.

The following Examples illustrate compositions according to the invention.

EXAMPLE A

Tablets containing 25 mg each of active ingredient and having the following composition are prepared by the usual technique:

| 2-hydroxyethyl 5-chloropyrid-2-yl dithiocarbamate | 25 mg |
|---|---|
| corn starch | 125 mg |
| colloidal silica | 45 mg |
| magnesium stearate | 5 mg |

EXAMPLE B

Tablets containing 25 mg each of active ingredient and having the following composition are prepared by the usual technique:

| 3-hydroxypropyl pyrid-2-yl dithiocarbamate | 25 mg |
|---|---|
| corn starch | 125 mg |
| colloidal silica | 45 mg |
| magnesium stearate | 5 mg |

We claim:

1. A compound of the formula:

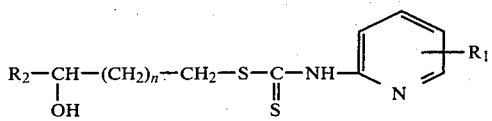

wherein $R_1$ represents a hydrogen atom and either
 (1) n is equal to 0 and $R_2$ represents a hydrogen atom, a hydroxymethyl, methylthiomethyl or phenyl radical, or
 (2) n is equal to 1 and $R_2$ represents a hydrogen atom or a phenyl radical; or $R_1$ represents a chlorine atom in the 5-position, n is equal to 0 or 1 and $R_2$ represents a hydrogen atom or a methyl, phenyl, fluorophenyl or methylphenyl radical, and when they exist, the optical isomers of the aforesaid compound.

2. A compound according to claim 1, in which n is 0 or 1, and either $R_1$ represents hydrogen in which case $R_2$ represents phenyl, or $R_1$ represents chlorine in the 5-position in which case $R_2$ represents hydrogen, methyl, phenyl, fluorophenyl, or methylphenyl.

3. A compound according to claim 1 in which $R_1$ represents hydrogen and either n is 0 and $R_2$ is hydrogen, hydroxymethyl, or methylthiomethyl, or n is 1 and $R_2$ is hydrogen.

4. A compound according to claim 1 which is 2-hydroxyethyl pyrid-2-yldithiocarbamate.

5. A compound according to claim 1 which is 2-hydroxyethyl 5-chloropyrid-2-yldithiocarbamate.

6. A compound according to claim 1 which is 3-hydroxypropyl pyrid-2-yldithiocarbamate.

7. A compound according to claim 1 which is 2,3-dihydroxypropyl pyrid-2-yldithiocarbamate.

8. A pharmaceutical composition useful as an anthelmintic comprising an effective amount of a compound as claimed in claim 1 in association with a compatible, pharmaceutically acceptable diluent or adjuvant.

9. A method of treating or preventing a helminth infection which comprises administering to a mammal suffering from or subject to a said infection an effective amount of a compound as claimed in claim 1.

* * * * *